(12) United States Patent
Lee

(10) Patent No.: US 11,536,635 B2
(45) Date of Patent: Dec. 27, 2022

(54) BIOLOGICAL MATERIAL, MEASURING INSTRUMENT

(71) Applicant: TASCOM CO., LTD., Anyang-si (KR)

(72) Inventor: Sung Dong Lee, Anyang-si (KR)

(73) Assignee: TASCOM CO., LTD., Anyang-si (KR)

( * ) Notice: Subject to any disclaimer, the term of this patent is extended or adjusted under 35 U.S.C. 154(b) by 112 days.

(21) Appl. No.: 15/737,414

(22) PCT Filed: Jun. 16, 2016

(86) PCT No.: PCT/KR2016/006409
§ 371 (c)(1),
(2) Date: Dec. 18, 2017

(87) PCT Pub. No.: WO2016/204533
PCT Pub. Date: Dec. 22, 2016

(65) Prior Publication Data
US 2018/0195938 A1    Jul. 12, 2018

(30) Foreign Application Priority Data

Jun. 16, 2015 (KR) .......................... 10-2015-0085372
Jun. 16, 2016 (KR) .......................... 10-2016-0075110

(51) Int. Cl.
*G01N 21/07* (2006.01)
*G01N 21/64* (2006.01)
(Continued)

(52) U.S. Cl.
CPC ........... *G01N 1/4077* (2013.01); *G01N 21/07* (2013.01); *G01N 21/31* (2013.01); *G01N 21/64* (2013.01);
(Continued)

(58) Field of Classification Search
None
See application file for complete search history.

(56) References Cited

U.S. PATENT DOCUMENTS 4,234,538 A * 11/1980 Ginsberg ............. G01N 21/253
250/226
6,285,450 B1   9/2001 Thomas et al.
(Continued)

FOREIGN PATENT DOCUMENTS

CN    202974847 U   6/2013
CN    104602725 A   5/2015
(Continued)

OTHER PUBLICATIONS

International Search Report dated Sep. 28, 2016, in corresponding International Application No. PCT/KR2016/006409 (2 pages in English, 3 pages in Korean).
(Continued)

*Primary Examiner* — Neil N Turk
(74) *Attorney, Agent, or Firm* — Insight Law Group, PLLC; Seung Lee

(57) ABSTRACT

A biological material measuring instrument is described. The biological material measuring instrument includes a rotating body and a main body. The rotating body includes one or more cartridge holders having cuvettes in which a reagent and an analyte in a sample react. The main body includes a pair of light-emitting parts and light-receiving parts to optically measure the analyte in the sample. The rotating body further includes a light-emitting optical waveguide for guiding the light of the light-emitting parts to the cuvette and a light-receiving optical waveguide for guiding.

20 Claims, 15 Drawing Sheets

(51) Int. Cl.
*G01N 35/04* (2006.01)
*G01N 35/02* (2006.01)
*G01N 35/00* (2006.01)
*G01N 1/40* (2006.01)
*G01N 21/31* (2006.01)
*G01N 21/76* (2006.01)
*G01N 33/49* (2006.01)
*B01L 3/00* (2006.01)
*G01N 21/03* (2006.01)
*B04B 5/04* (2006.01)

(52) U.S. Cl.
CPC ......... *G01N 21/6428* (2013.01); *G01N 21/76* (2013.01); *G01N 33/491* (2013.01); *B04B 5/0407* (2013.01); *G01N 2001/4083* (2013.01); *G01N 2021/0325* (2013.01); *G01N 2021/0378* (2013.01); *G01N 2035/00504* (2013.01); *G01N 2201/0423* (2013.01); *G01N 2201/08* (2013.01); *G01N 2201/0846* (2013.01)

(56) References Cited

U.S. PATENT DOCUMENTS

| | | | |
|---|---|---|---|
| 8,344,334 | B2 | 1/2013 | Coker et al. |
| 9,594,020 | B2 | 3/2017 | Koudelka et al. |
| 10,209,185 | B2 | 2/2019 | Koudelka et al. |
| 2002/0155619 | A1 | 10/2002 | Kurihara et al. |
| 2004/0265173 | A1* | 12/2004 | Matsumoto .......... G01N 35/025 422/64 |
| 2006/0198759 | A1 | 9/2006 | Shneider et al. |
| 2009/0021741 | A1 | 1/2009 | Kim et al. |
| 2009/0308746 | A1 | 12/2009 | Hwang et al. |
| 2011/0051133 | A1 | 3/2011 | Ogawa |
| 2011/0093207 | A1 | 4/2011 | Ingber et al. |
| 2011/0293479 | A1 | 12/2011 | Hong et al. |
| 2012/0003731 | A1 | 1/2012 | Kuroda |
| 2012/0293796 | A1* | 11/2012 | Ludowise .............. G01N 35/04 356/244 |
| 2013/0034466 | A1* | 2/2013 | Wakamiya ....... G01N 35/00584 422/64 |
| 2019/0120761 | A1 | 4/2019 | Koudelka et al. |

FOREIGN PATENT DOCUMENTS

| | | |
|---|---|---|
| JP | 2007-218633 A | 8/2007 |
| JP | 2009-281941 A | 12/2009 |
| KR | 10-2009-0128891 A | 12/2009 |
| KR | 10-2010-0008476 A | 1/2010 |
| KR | 10-2013-0072987 A | 7/2013 |
| KR | 10-1365939 B1 | 2/2014 |
| KR | 10-2014-0122832 A | 10/2014 |
| WO | WO 2009/047549 A1 | 4/2009 |

OTHER PUBLICATIONS

Extended European Search Report dated Oct. 30, 2018 in corresponding European Application No. 16811946.9 (20 pages in English).
European Office Action dated Jun. 18, 2019 in counterpart European Patent Application No. 16811946.9 (6 pages in English).
Chinese Office Action dated Dec. 23, 2019 in counterpart Chinese Patent Application No. 201680046212.0 (6 pages in Chinese).

* cited by examiner

BIOLOGICAL MATERIAL, MEASURING INSTRUMENT

CROSS REFERENCE TO RELATED APPLICATION(S)

This application is a U.S. National Stage Application of International Application No. PCT/KR2016/006409, filed on Jun. 16, 2016 and published as WO 2016/204533 on Dec. 22, 2016. This application and PCT/KR2016/006409 claim the benefit under 35 USC 119(a) and 365(b) of Korean Patent Application Nos. 10-2015-0085372 filed on Jun. 16, 2015 and 10-2016-0075110 filed on Jun. 16, 2016 in the Korean Intellectual Property Office. The disclosures of PCT/KR2016/006409 and Korean Patent Application Nos. 10-2015-0085372 and 10-2016-0075110 are incorporated herein by reference.

TECHNICAL FIELD

The present invention relates to a bioinstrument.

BACKGROUND ART

To accurately measure analytes in human-, animal-, and environment-derived samples using a spectroscopic method such as spectrophotometry, a fluorescence method, a chemiluminescence method, or the like, particle components present in samples must be removed. The particle components present in samples include blood cell components such as red blood cells, white blood cells, platelets, and the like, lipoproteins, particles present in stool, particle components present in environmental samples, and the like, and include magnetic particles, latex particles, silica particles, and the like that are artificially added together with samples. When these particles co-exist in a sample, the turbidity of a solution is exhibited in spectroscopic measurement, or phenomena such as light scattering, light absorption, and the like are caused, and thus it is difficult to accurately measure light. Generally, a centrifugation method is used as a method of removing particle components present in a sample. The centrifugation method is a method in which a sample contained in a vessel is rotated to precipitate particle components by centrifugal force.

Meanwhile, Korean Registered Patent Publication No. 10-1365939 discloses an invention relating to a cartridge for the measurement of a biological sample component and an apparatus for measuring a biological sample component, and discloses a diagnostic instrument capable of transferring and mixing a desired reagent and sample by actively manipulating a fluid to measure the amounts of microalbumin and creatinine during urination.

DISCLOSURE

Technical Problem

An object of the present invention is to provide a bioinstrument capable of separating a particle component from a sample using centrifugal force, and preventing the separated particle component from interfering with spectroscopic measurement.

Technical Solution

According to one aspect of the present invention, a bioinstrument includes a rotating body including one or more cartridge holders to allow a cuvette to be loaded therein, the cuvette allowing a reaction between a reagent and an analyte in a sample, and a main body including at least a pair of a light emitting part and a light receiving part that are configured to optically measure the analyte in the sample, wherein the rotating body further includes: a light emitting optical waveguide to guide light of the light emitting part to a light irradiation surface, the light irradiation surface being one surface of the cuvette except for a sample introduction surface of the cuvette into which the sample is introduced, and a centrifugal force acting surface of the cuvette on which a particle component in the sample is separated from the sample and adsorbed or precipitated by centrifugal force generated according to rotation of the rotating body; and a light receiving optical waveguide to guide light having passed through a light receiving measurement surface to the light receiving part, the light receiving measurement surface being one surface of the cuvette except for the sample introduction surface and the centrifugal force acting surface.

According to one embodiment, the light irradiation surface of the light receiving measurement surface of the cuvette face each other.

According to one embodiment, the light irradiation surface of the light receiving measurement surface of the cuvette face each other at right angles.

Meanwhile, a bioinstrument according to one aspect includes a rotating body including one or more cartridge holders to allow a cuvette to be loaded therein, the cuvette allowing a reaction between a reagent and an analyte in a sample, and a main body including at least a pair of a light emitting part and a light receiving part that are configured to optically measure the analyte in the sample, wherein the rotating body further includes a light receiving optical waveguide to guide light having passed through a light receiving measurement surface to the light receiving part, the light receiving measurement surface being one surface of the cuvette except for a sample introduction surface of the cuvette into which the sample is introduced, and a centrifugal force acting surface of the cuvette on which a particle component in the sample is separated from the sample and adsorbed or precipitated by centrifugal force generated according to rotation of the rotating body.

Advantageous Effects

According to the disclosed invention, a particle component can be separated from a sample using centrifugal force and the separated particle component can be prevented from interfering with spectroscopic measurement.

MODE OF THE INVENTION

The foregoing and additional aspects of the present invention will become more apparent through exemplary embodiments that will be described with reference to the accompanying drawings. Hereinafter, the present invention will be described in detail in such a way that the invention may be easily understood and carried out by those skilled in the art through these embodiments.

Figure 1:
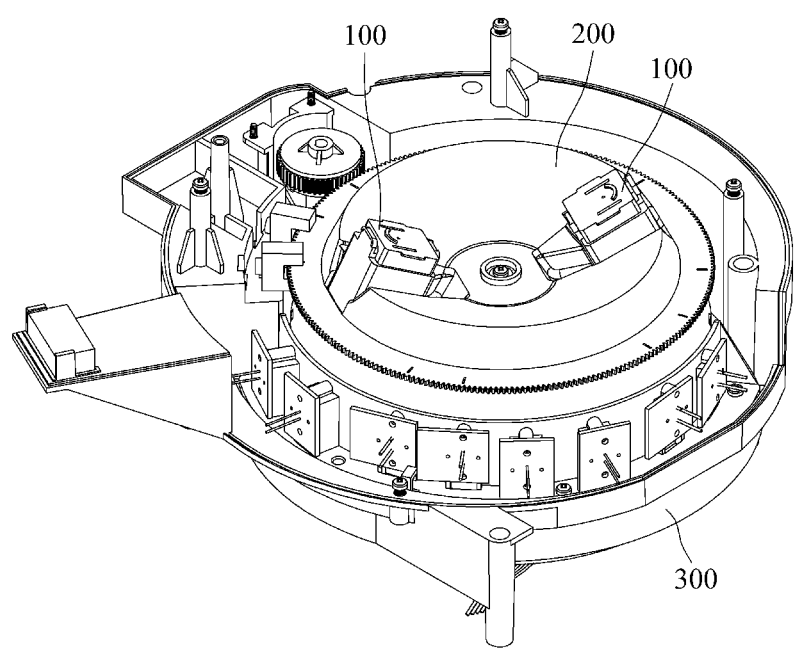
FIG. 1 is a perspective view of a bioinstrument according to an embodiment.
Figure 2:
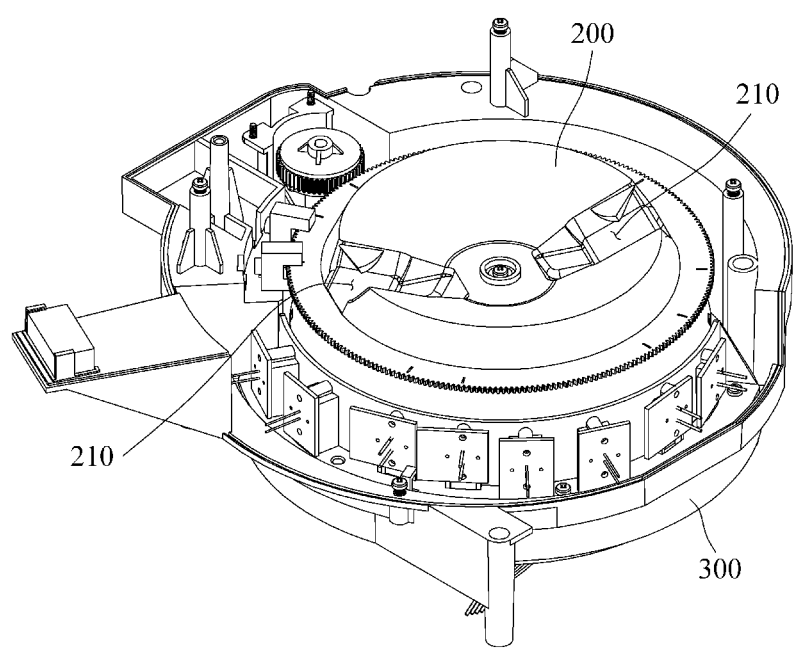
FIG. 2 is a perspective view illustrating a state in which a measurement cartridge of FIG. 1 is removed.
Figure 3:
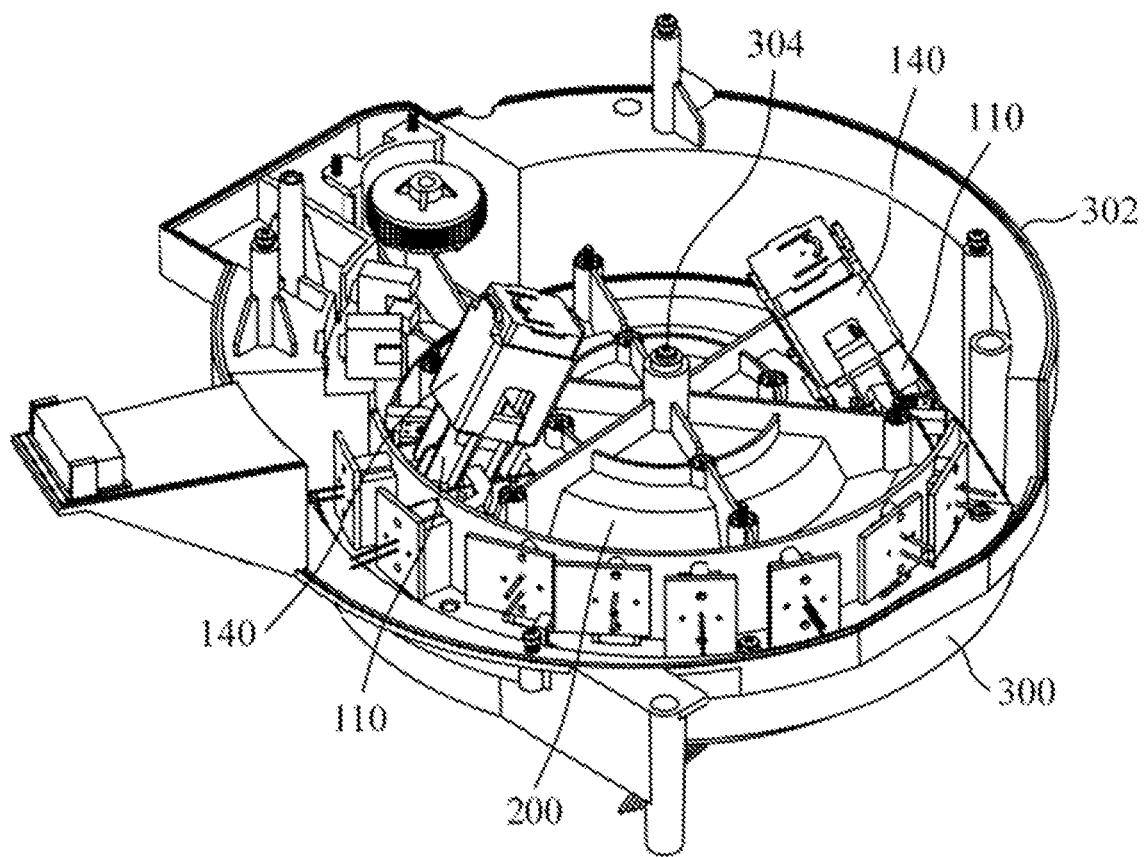
FIG. 3 is a perspective view illustrating a state in which an upper portion of a rotating body of FIG. 1 is removed.
Figure 4:
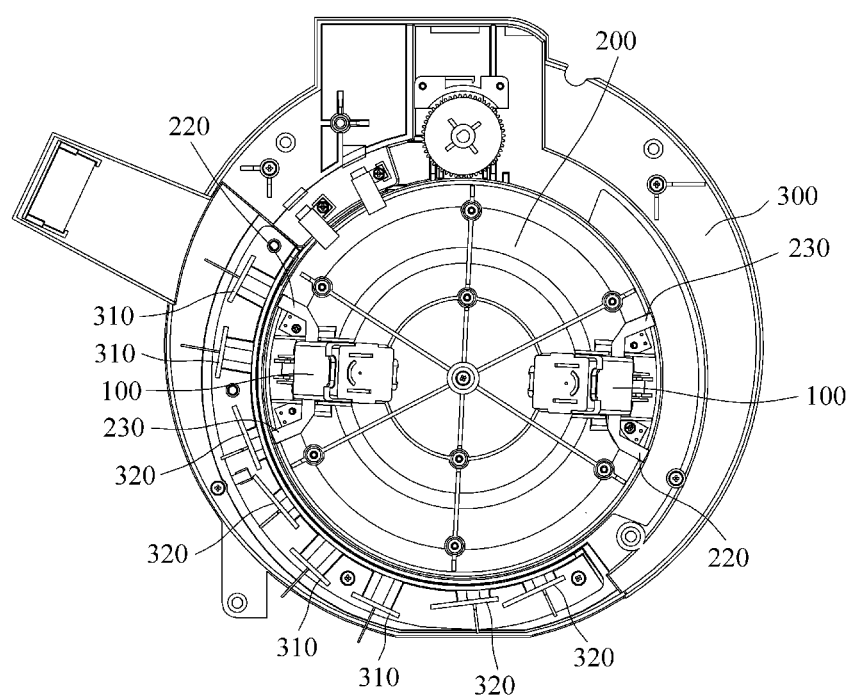
FIG. 4 is a plan view of FIG. 3.
Figure 5:
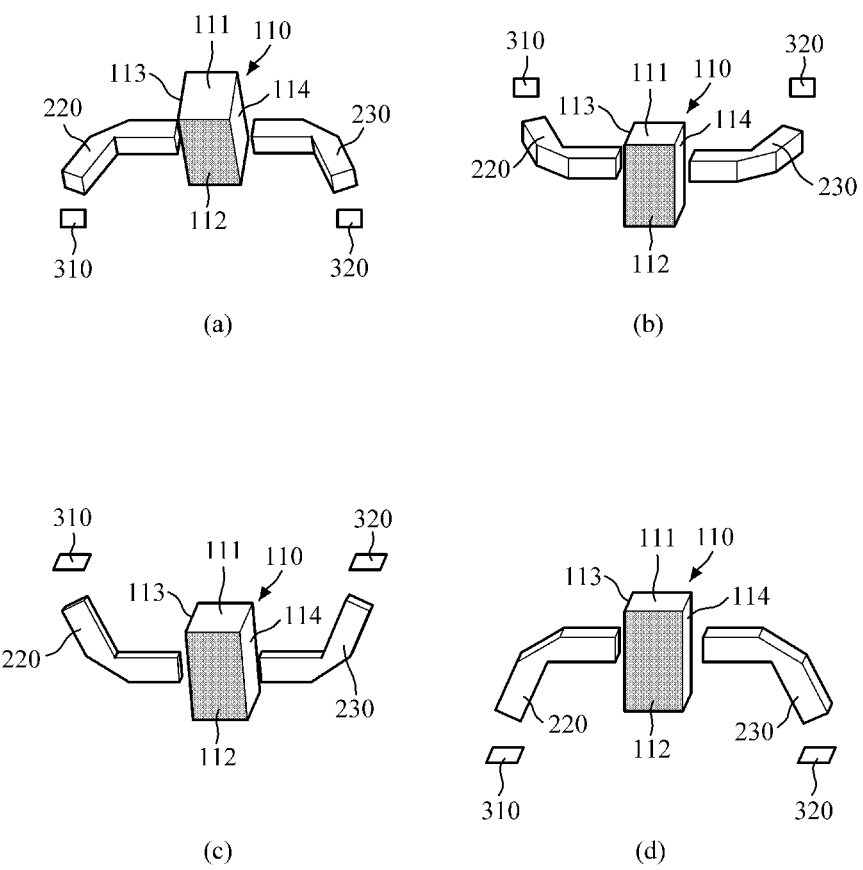
FIG. 5 exemplarily illustrates positions of a light emitting part and a light receiving part.
Figure 6:
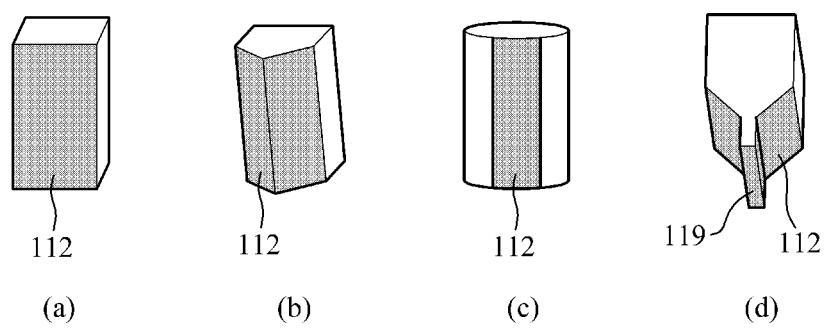
FIG. 6 exemplarily illustrates a shape of a cuvette.
Figure 7:
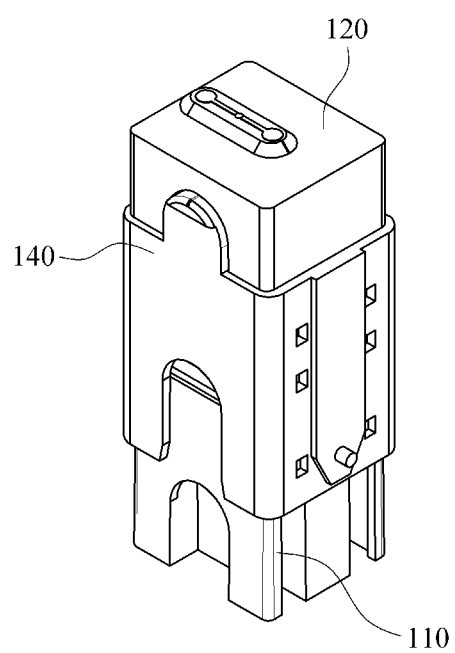
FIG. 7 is a perspective view of a measurement cartridge according to an embodiment.
Figure 8:
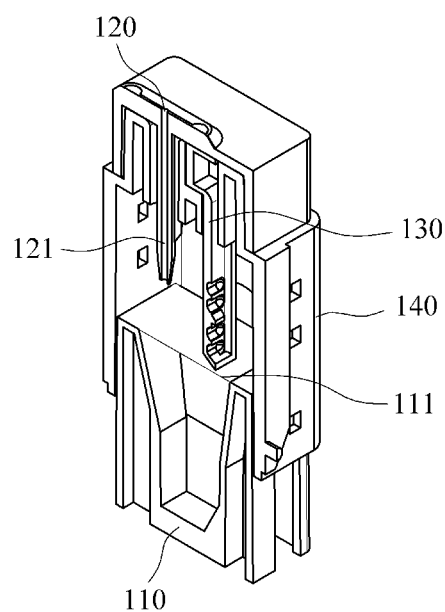
FIG. 8 is a cross-sectional view of the measurement cartridge according to an embodiment.

FIG. 1 is a perspective view of a bioinstrument according to an embodiment. FIG. 2 is a perspective view illustrating a state in which a measurement cartridge of FIG. 1 is removed. FIG. 3 is a perspective view illustrating a state in which an upper portion of a rotating body of FIG. 1 is removed. FIG. 4 is a plan view of FIG. 3. FIG. 5 exemplarily illustrates positions of a light emitting part and a light receiving part. FIG. 6 exemplarily illustrates a shape of a cuvette. A rotating body 200 is supported by a main body 300, and is an instrument connected to a motor to be rotatable. The rotating body 200 includes one or more cartridge holders 210. A cartridge 100 in which a liquid reagent and an analyte in a sample react is installed in the cartridge holder 210. FIG. 7 is a perspective view of a measurement cartridge according to an embodiment. FIG. 8 is a cross-sectional view of the measurement cartridge according to an embodiment. A cuvette 110 is a container for allowing a reaction between a reagent and a sample. A surface of the cuvette 110 is sealed with a film. A sealing film 117 seals the cuvette 110 to prevent a liquid reagent stored in the cuvette 110 from being leaked and evaporated, and the sample or the reagent is introduced into the cuvette 110 through rupture of the sealing film 117. In addition, a measurement cartridge 100 may include a capillary module 120 for collecting a sample and a reagent rod 130 for storing a drying reagent. The capillary module 120 is filled in a capillary form with a sample to be analyzed, and is installed in a housing 140 in a state of being filled with the sample. In addition, the reagent rod 130 stores one or more drying reagents, and is installed at the housing 140.

Referring back to FIG. 1, the main body 300 is spaced apart from the rotating body 200 and includes at least a pair of a light emitting part 310 and a light receiving part 320 that are fixed to the main body 300. The light emitting part 310 may be a light emitting diode (LED), and the light receiving part 320 may be a photodiode (PD). To measure an analyte in a sample using a spectroscopic method such as spectrophotometry, a fluorescence method, a chemiluminescence method, or the like, the light emitting part 310 serves to emit light to the cuvette 110, and the light receiving part 320 serves to receive light from the cuvette 110. The light emitting part 310 and the light receiving part 320 may be configured in multiple pairs, and, in this case, the light emitting parts 310 may have different light wavelengths. Thus, in a case in which absorbance is measured for one cuvette, the measurement of absorbance at various wavelengths is possible.

Although not shown in the drawings, the main body 300 also includes one or more motors for rotating the rotating body 200, and a control module for optical measurement and overall control. The control module may rotate the rotating body 200 at a high speed by driving the motor, and may also transfer the cuvette 110 to an optical measurement space by rotating the rotating body 200. As used herein, the optical measurement space refers to a predetermined space that allows the pair of the light emitting part 310 and the light receiving part 320 to emit light to the cuvette 110 and receive light therefrom.

The cuvette 110 is a container that may be made of a transparent plastic and allows a reaction between a liquid reagent and an analyte in a sample. The cuvette 110 may have a polygonal column shape such as a rectangular column shape, a right triangular shape, or the like, or a cylindrical shape, and may have a combination of these shapes. The cuvette 110 includes a sample introduction surface 111 and a centrifugal force acting surface 112. The sample introduction surface 111 is a surface that allows the sample to be introduced into the cuvette 110, and is preferably an upper surface. In particular, the sample introduction surface 111 refers to a surface having an opening sealed by a sealing film. The sealing film 117 is ruptured and, as a result, the sample may be introduced into the cuvette 110. The cuvette 110 may be rotatably installed in the cartridge holder 210 of the rotating body 200, and a particle component in the sample is precipitated or adsorbed on a surface of the cuvette 110 by centrifugal force generated by rotation thereof. In this regard, a surface on which a particle component is precipitated or adsorbed is referred to as the centrifugal force acting surface 112.

Meanwhile, to measure an analyte in a sample, a process of separating a particle component from the sample is required. In this regard, the particle component refers to blood cells such as red blood cells, white blood cells, and the like. The separation of the particle component may be achieved by centrifugal force generated according to rotation of the rotating body 200, and the particle component separated from the sample are precipitated or adsorbed on the above-described centrifugal force acting surface 112 by the generated centrifugal force. Theoretically, the centrifugal force acting surface 112 is a surface facing an outer side of the rotating body 200. Thus, light must avoid the sample introduction surface 111 and the centrifugal force acting surface 112.

When the sample introduction surface 111 is an upper surface, one of the light emitting part 310 and the light receiving part 320 may be positioned to face one side surface of the cuvette 110 inside the rotating body 200 and the other thereof may be positioned to face an opposite side surface of the cuvette 110 outside the rotating body 200, whereby the sample introduction surface 111 may be avoided. However, the centrifugal force acting surface 112 necessarily becomes a surface facing an outer side of the rotating body 200, and thus the centrifugal force acting surface 112 cannot be avoided. This means that light must pass through the centrifugal force acting surface 112, but the particle component precipitated or adsorbed on the centrifugal force acting surface 112 may interfere with light transmission. Accordingly, optical measurement results cannot be secured.

To secure optical measurement results, the rotating body 200 according to an embodiment further includes one or more optical waveguides. The optical waveguide is installed in the cartridge holder 210 of the rotating body 200 in surface contact therewith to face a surface of the cuvette 110, and serves to irradiate the surface thereof with light or receive light having passed through the surface thereof. The optical waveguide is positioned to face a surface except for the sample introduction surface 111 and the centrifugal force acting surface 112 of the cuvette 110. As illustrated in FIG. 4, the rotating body 200 may include a light emitting optical waveguide 220 and a light receiving optical waveguide 230. The rotating body 200 may include only the light receiving optical waveguide 230. The light emitting optical waveguide 220 faces a light irradiation surface 113 of the cuvette 110, and the light receiving optical waveguide 230 faces a light receiving measurement surface 114 of the cuvette 110. In this regard, the light irradiation surface 113 and the light receiving measurement surface 114 are surfaces except for the sample introduction surface 111 and the centrifugal force acting surface 112. The light emitting optical waveguide 220 and the light receiving optical waveguide 230, which are installed in the rotating body 200, are positioned to correspond to the light emitting part 310 and the light receiving part 320 through control of the position of the rotating body 200, and thus serve to transmit incident light from the light emitting part 310 to the light irradiation surface 113 of the cuvette 110, and collect light from the light receiving measurement surface 114 of the cuvette 110 and transmit the light to the light receiving part 320.

Since the optical waveguide can change a path of light, the light emitting part 310 and the light receiving part 320 may be variously positioned. FIG. 5(*a*) illustrates a case in which the light emitting part 310 and the light receiving part 320 are positioned in a direction in which centrifugal force acts on the cuvette 110, i.e., outside the rotating body 200. FIG. 5(*b*) illustrates a case in which the light emitting part 310 and the light receiving part 320 are positioned in a direction opposite to the direction in which centrifugal force acts on the cuvette 110, i.e., inside of the rotating body 200. FIG. 5(*c*) illustrates a case in which the light emitting part 310 and the light receiving part 320 are positioned in a direction opposite to a gravitational direction, and FIG. 5(*d*) illustrates a case in which the light emitting part 310 and the light receiving part 320 are positioned in a downward direction, i.e., a direction in which gravity acts on the cuvette 110. In addition, the above positions of the light emitting part 310 and the light receiving part 320 may be combined. In one embodiment, the light emitting part 310 may be positioned in the direction in which centrifugal force acts on the cuvette 110, and the light receiving part 320 may be positioned in a direction opposite thereto.

As illustrated in FIGS. 1 to 3, inner walls of the cartridge holders 210 of the rotating body 200 are configured to be inclined with respect to a rotational axis or axle 304 of the rotating body 200 so that the cartridge 100 is loaded to be inclined towards the inside of the rotating body 200. The rotational axis or axle 304 is disposed in the enclosure 302. Accordingly, a bottom surface of the cuvette 110 may be the centrifugal force acting surface 112.

In the case of absorbance measurement, the light irradiation surface 113 and the light receiving measurement surface 114 are surfaces facing each other. In the case of fluorescence measurement, excitation light is emitted to the light irradiation surface 113 of the cuvette 110 and emission light generated by a fluorescent material or phosphorescent material present in the cuvette 110 is measured in the light receiving measurement surface 114. Unlike absorbance measurement, in fluorescence measurement, the excitation light and the emission light may be perpendicular to each other. Thus, the light irradiation surface 113 and the light receiving measurement surface 114 are surfaces facing each other at right angles. In addition, in the case of chemiluminescence measurement, light is emitted by a reaction inside the cuvette 110, and thus the light emitting optical waveguide 220 is not needed and only the light receiving optical waveguide 230 is used. Thus, when using different measurement methods for each cartridge holder 210, an optical waveguide may be configured in accordance with any one of absorbance measurement, fluorescence measurement, and chemiluminescence measurement according to each cartridge holder 210.

According to one embodiment, a light emitting part and a light receiving part measure luminance of a measurement surface. The measurement of spectroscopic characteristics requires a complicated and expensive sensor, but luminance measurement may be performed using an inexpensive light emitting diode and photo detector. The measurement of luminescence by fluorescence or phosphorescence is performed by measuring the intensity of luminescence by electromagnetic waves with a very narrow band and a single frequency/wavelength, and thus quantitative analysis is possible only with luminance detection.

According to one embodiment, a light emitting part of a main body may include a plurality of light emitting parts with different wavelength bands. For example, in the embodiment illustrated in FIGS. 1 to 3, two cuvettes may be installed at the rotating body 200, but a greater number of light emitting parts and light receiving parts may be installed at the main body along an outer circumference of the rotating body 200. In this case, a plurality of light emitting part-light receiving part pairs may have appropriate frequencies or wavelengths according to an object to be measured. For example, a first light emitting part-light receiving part pair may use light with a wavelength of 630 nm, and a second light emitting part-light receiving part pair may use light with a wavelength of 800 nm. A third light emitting part-light receiving part pair may use light with a wavelength of 300 nm. When the object to be measured is changed, the rotating body is rotated to a position of an appropriate light emitting part-light receiving part pair in accordance therewith and cuvettes are aligned, and measurement may be performed at the corresponding frequency or wavelength.

In addition, as illustrated in FIGS. 6(*a*), 6(*b*), 6(*c*), and 6(*d*), the cuvettes 110 installed at the rotating body 200 may have various shapes. A particle component in a sample is separated from a solution by centrifugal force and may be precipitated or adsorbed on the centrifugal force acting surface 112 of the cuvette 110. In addition, the number of the centrifugal force acting surfaces 112 may be one or more according to the shape of the cuvette 110. In addition, the centrifugal force acting surface 112 may be a plane, a line, or a dot according to the shape of the cuvette 110. The particle component in a sample may be completely or partially adsorbed or precipitated on the centrifugal force acting surface 112 of the cuvette 110 by centrifugal force generated according to rotation. In addition, as illustrated in FIG. 6(*d*), the cuvette 110 may be provided with a particle collector 119 capable of collecting a particle component. The particle collector 119 may be formed on a surface of the cuvette 110 on which centrifugal force acts, and may have an uneven structure or a form with grooves to collect a particle component.

Meanwhile, to separate a particle component present in a sample from a solution by centrifugal force, high-speed rotation is required, and to rotate the rotating body 200 at a high speed, the rotating body 200 is connected to a motor for rotation control such as a DC motor, a brushless DC (BLDC) motor, an AC motor, an induction motor, a stepping motor, or the like, and may be rotated at 1,000 rpm (revolutions per minute) or more. In addition, to irradiate the light irradiation surface 113 of the cuvette 110 with light from the light emitting part 310 via the light emitting optical waveguide 220 included in the rotating body 200 or to transmit light collected from the light receiving measurement surface 114 of the cuvette 110 to the light receiving part 320, it is important to accurately control the position of the rotating body 200. For this, the rotating body 200 may be further connected to a stepping motor. The stepping motor is used as a motor for position control to accurately control the position of the rotating body 200, and may be connected to the rotating body 200 only in a process for optical measurement.

When drying reagent accommodation parts 131 and 132 of the capillary module 120 or the reagent rod 130 pass through the sealing film 117 that seals the cuvette 110 and are introduced into the cuvette 110 by pressure applied to the capillary module 120 or the reagent rod 130 constituting a part of the cartridge 100, the rotating body 200 is rotated in one direction or leftward and rightward to cause centrifugal force and, as a result, a sample collected in the capillary module 120 is introduced into the cuvette 110. When the sample is introduced into the cuvette 110, the rotating body 200 is rotated leftward and rightward to mix the sample with a liquid reagent present in the cuvette 110. In one embodiment, when the sample is whole blood including blood cells, the sample and the liquid reagent are mixed in the cuvette 110, and then hematocrit measurement is possible using an absorbance measurement method. In addition, to separate red blood cells, which are a particle component present in the whole blood sample, from a liquid reagent inside the cuvette 110, the rotating body 200 is rotated at a high speed. The rotating body 200 should induce sufficient centrifugal force to centrifuge the red blood cells, and should be rotated at 1,000 rpm or more. The red blood cells are precipitated or adsorbed on the centrifugal force acting surface 112 of the cuvette 110 by high-speed rotation of the rotating body 200.

The reagent rod 130 and the capillary module 120, which are installed at an upper side of the housing 140, and the cuvette 110 and the sealing film 117, which are installed at a lower end side of the housing 140, will now be described with reference to FIG. 8. As illustrated in the drawing, the reagent rod 130 is vertically spaced apart from the sealing film 117 of the cuvette 110, and the capillary module 120 is vertically spaced apart from the sealing film 117. According to one embodiment, a tip of a reagent rod is configured longer than that of a capillary module, and thus reaches closer to the sealing film 117.

Figure 9:
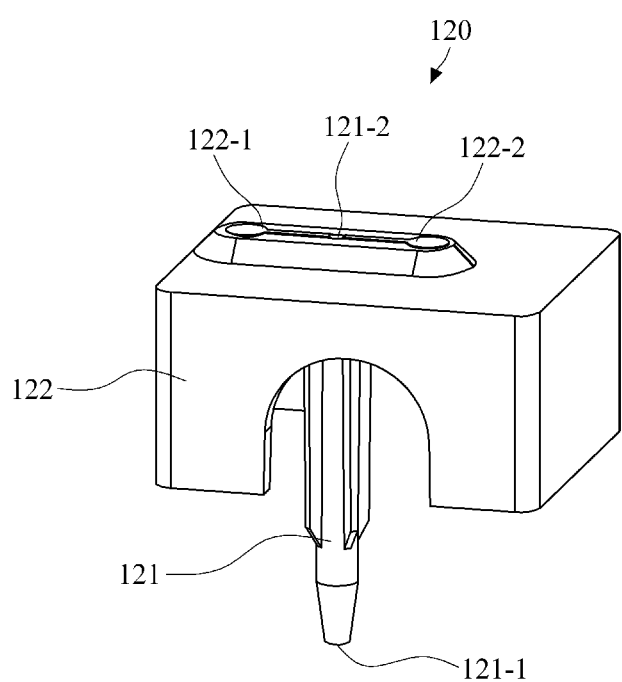
FIG. 9 is a perspective view of a capillary module according to an embodiment.
Figure 10:
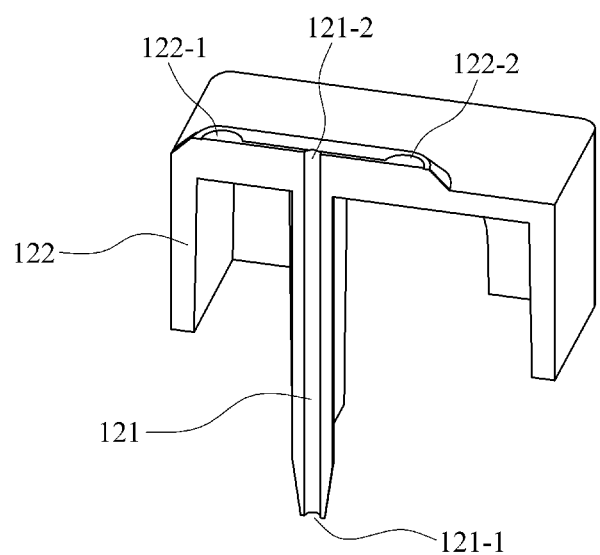
FIG. 10 is a perspective view illustrating a section of the capillary module according to an embodiment.

FIG. 9 is a perspective view of the capillary module 120 according to an embodiment. FIG. 10 is a cross-sectional view of the capillary module 120 according to an embodiment. The capillary module 120 includes a capillary tube 121 to collect a liquid sample using capillary action, and a body 122 configured integrally with the capillary tube 121. One end of the capillary tube 121 is a sample introduction part 121-1 configured to initially come into contact with a sample. In addition, the capillary tube 121 may have, at the other end thereof, an air discharge part 121-2 to discharge air inside the capillary tube 121 in a process in which the sample is introduced into the capillary tube 121. When the sample introduction part 121-1 comes into contact with the sample, the sample is introduced into the capillary tube 121 by capillary action. To easily introduce the sample by capillary action, an inner wall of the capillary tube 121 may be treated with a surfactant to have hydrophilic properties.

The air discharge part 121-2 of the capillary tube 121 is exposed at an upper surface of the body 122. When the body 122 is pressed, the capillary tube 121 is moved downward, and the capillary tube 121 passes through the sealing film 117 of the cuvette 110 and moves into the cuvette 110. At this time, a rupture portion of the sealing film 117 may be limited only to a portion coming into contact with the capillary tube 121. That is, a film formed of an appropriate material may be selected so that the rupture portion of the sealing film 117 corresponds only to a portion thereof coming into contact with the capillary tube 121 when the capillary tube 121 passes through the sealing film 117 by pressure applied to the body 122. When the rupture portion of the sealing film 117 is minimized to the portion thereof coming into contact with the capillary tube 121, the sample smeared on an outer surface of the capillary tube 121 may be filtered by the sealing film 117 contacting the outer surface. In a case in which the sample smeared on the outer surface of the capillary tube 121 is introduced into the cuvette 110, a total amount of the sample introduced into the cuvette 110 exceeds an appropriate amount, and thus an error may be caused in measurement results, and, therefore, only an appropriate amount of the sample may be introduced into the cuvette 110 by filtering the sample smeared on the outer surface of the capillary tube 121, thereby preventing measurement errors.

In addition, a first sample recognition electrode 122-1 and a second sample recognition electrode 122-2 may be formed at an upper surface of the body 122. The first sample recognition electrode 122-1 and the second sample recognition electrode 122-2 are separate from each other, and come into contact with the air discharge part 121-2. The first sample recognition electrode 122-1 and the second sample recognition electrode 122-2 are configured to prevent a sample collected in an insufficient amount due to a user's mistake from being measured. Such sample recognition electrodes may be formed by printing conductive ink such as Ag, AgCl, carbon, graphite, Cu, or the like, or may be formed by sputtering of a conductive material such as Au, indium tin oxide (ITO), or the like. In one embodiment, resistance or conductivity between the first sample recognition electrode 122-1 and the second sample recognition electrode 122-2 is measured in a process in which the sample introduction part 121-1 of the capillary tube 121 passes through the sealing film 117.

Figure 11:
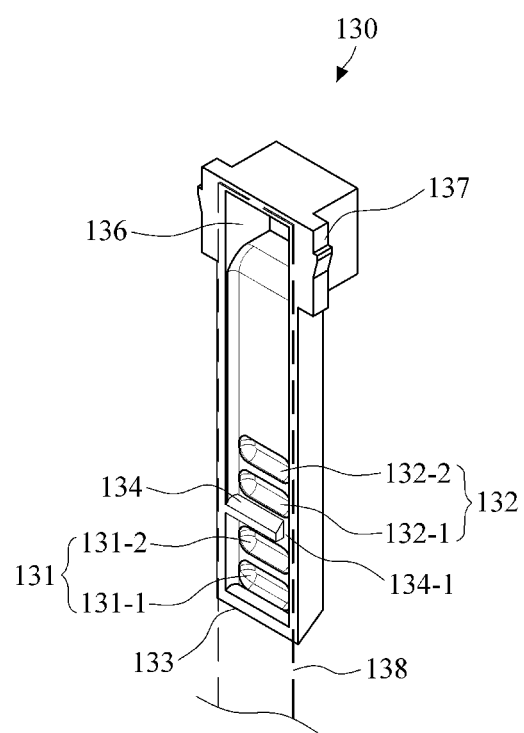
FIG. 11 is a perspective view of a reagent rod according to an embodiment.

FIG. 11 is a perspective view of the reagent rod 130 according to an embodiment. The reagent rod 130 may include a lower drying reagent accommodation part 131 and an upper drying reagent accommodation part 132 that are arranged on the same plane. The lower drying reagent accommodation part 131 may include a 1-1 drying reagent accommodation part 131-1 and a 1-2 drying reagent accommodation part 131-2, and the upper drying reagent accommodation part 132 may include a 2-1 drying reagent accommodation part 132-1 and a 2-2 drying reagent accommodation part 132-2. The reagent rod 130 may be provided, at a lower portion thereof, with a rupture portion 133 to rupture the sealing film 117, and may be provided, at an upper portion thereof, with a desiccant accommodation part 136 to accommodate a desiccant. In addition, the reagent rod 130 may further include a solution blocking part 134 between the lower drying reagent accommodation part 131 and the upper drying reagent accommodation part 132.

In addition, the reagent rod 130 may further include a reagent rod sealing film 138. The reagent rod sealing film 138 seals at least a part of the reagent rod 130, including the lower drying reagent accommodation part 131 and the upper drying reagent accommodation part 132. In addition, the reagent rod sealing film 138 may also seal the desiccant accommodation part 136 together therewith. To maintain low humidity of the lower and upper drying reagent accommodation parts 131 and 132 in a state of being sealed by the reagent rod sealing film 138, an air path 134-1 to allow air to move therethrough may be formed in a part of the solution blocking part 134. The desiccant accommodation part 136 and the lower and upper drying reagent accommodation parts 131 and 132 are connected to one another through the air path 134-1 so as to allow fluid flow therebetween.

The reagent rod sealing film 138 may extend from the reagent rod 130, and an end of the extended portion thereof may be attached to the housing 140. In one embodiment, the end of the extended portion thereof may be attached to an outer wall of the housing 140. This is configured so that the reagent rod sealing film 138 is automatically stripped when the reagent rod 130 is introduced into the cuvette 110. The end of the extended portion thereof may also be attached to the cuvette 110. This is also configured so that the reagent rod sealing film 138 is automatically stripped when the reagent rod 130 is introduced into the cuvette 110. In another embodiment, a user may directly strip the reagent rod sealing film 138 for use. Meanwhile, an assembly guiding part 137 is a guiding part when the reagent rod 130 is assembled to the housing 140.

Figure 12:
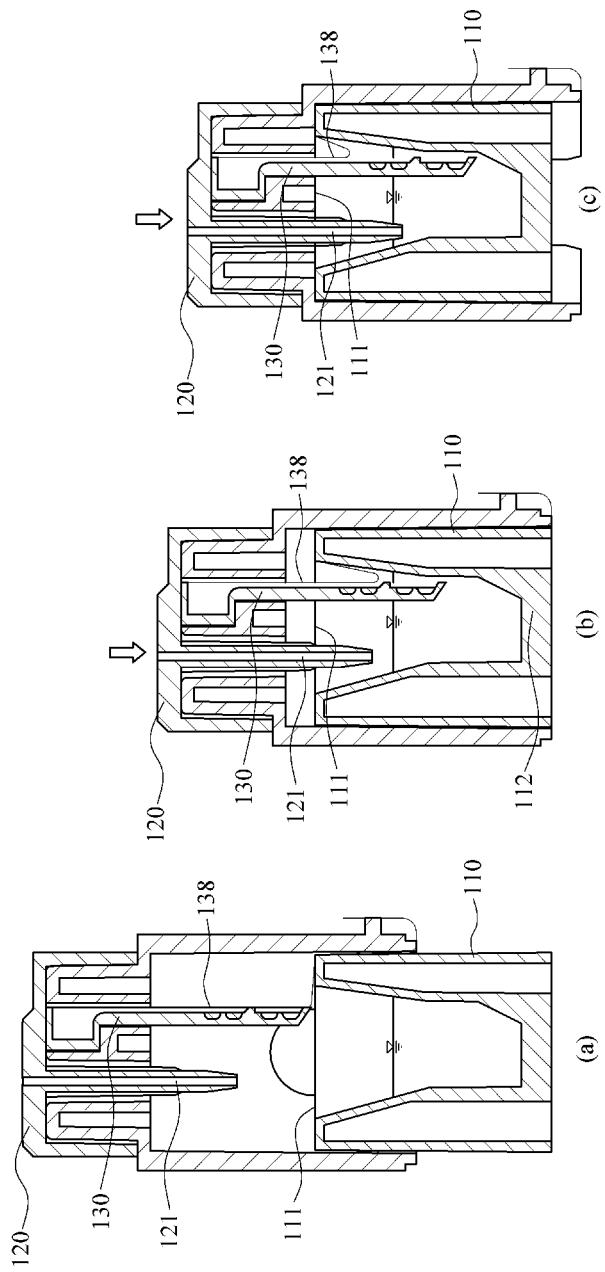
FIG. 12 illustrates reference views for explaining an operation of the measurement cartridge according to an embodiment.

FIG. 12 illustrates reference views for explaining an operation of a measurement cartridge according to an embodiment. FIG. 12(a) illustrates a state in which the housing 140 including the capillary module 120 and the reagent rod 130 is installed from an upper side of the cuvette 110. At this time, both the capillary tube 121 of the capillary module 120 and the reagent rod 130 are in a state of being positioned above the sealing film 117 of the cuvette 110. When a primary pressure is applied to the housing 140 in this case, the housing 140 is moved downward. Accordingly, the capillary tube 121 of the capillary module 120 and the reagent rod 130 pass through the sealing film 117 and are introduced into the cuvette 110.

According to one embodiment, when pressure is applied to the housing 140, the reagent rod 130 separated from the sealing film 117 by a relatively closer distance first passes through the sealing film 117 and is introduced into the cuvette 110, and then the capillary module 120 is introduced thereinto. When the cuvette 110 including a liquid reagent is exposed to a high temperature or a low pressure environment in a state of being sealed by the sealing film 117, pressure is generated inside the sealed cuvette 110. In a case in which the sample introduction part 121-1 of the capillary module 120 passes through the sealing film 117 and is introduced into the cuvette 110 in a state in which pressure has been generated inside the cuvette 110, the sample that fills the capillary tube 121 may be discharged to the outside via an air discharge part while the pressure is discharged to the air discharge part via the sample introduction part 121-1 of the capillary module 120. For example, a sample such as blood to be measured may be ejected outside the cuvette 110, thus causing infection problems. Thus, the tip of the reagent rod 130 may first rupture the sealing film 117 before the tip of the capillary module 120 does to discharge the pressure generated inside the cuvette 110, and then the capillary module 120 may rupture the sealing film 117 and may be introduced into the cuvette 110.

Referring to FIG. 12(b), only the reagent rod sealing film 138 at the lower drying reagent accommodation part 131 may be stripped by adjusting a pressing depth. Thereafter, as illustrated in FIG. 12(c), when a secondary pressure is applied to the housing 140, the reagent rod 130 is further moved downward, and, accordingly, the reagent rod sealing film 138 at the upper drying reagent accommodation part 132 is also stripped. That is, the lower drying reagent accommodation part 131 and the upper drying reagent accommodation part 132 may be configured to be exposed sequentially. In addition, the lower drying reagent accommodation part 131 and the upper drying reagent accommodation part 132 may be configured to be exposed at once by adjusting a pressing depth.

Figure 13:
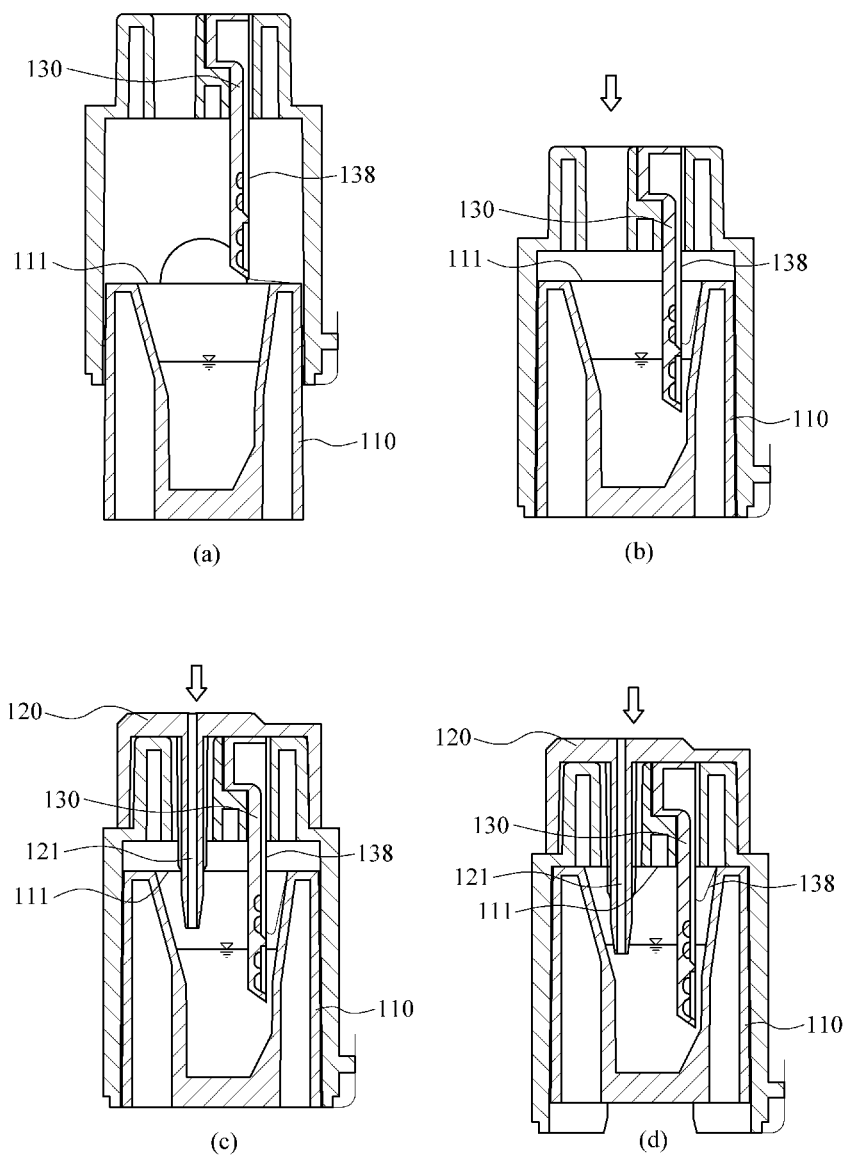
FIG. 13 illustrates reference views for explaining an operation of a measurement cartridge according to another embodiment.

FIG. 13 illustrates reference views for explaining an operation of a measurement cartridge according to another embodiment. FIG. 13(a) illustrates a state in which the housing 140 is installed from an upper side of the cuvette 110. In this state, only the reagent rod is installed in the housing 140 and the capillary module 120 is not installed. When a primary pressure is applied to the housing 140 in this state, as illustrated in FIG. 13(b), the housing 140 is moved downward. Accordingly, the reagent rod 130 passes through the sealing film 117 and is introduced into the cuvette 110. Referring to FIG. 13(b), only the reagent rod sealing film at the lower drying reagent accommodation part 131 may be stripped by adjusting a pressing depth. Thereafter, when the capillary module 120 is installed in the housing 140, as illustrated in FIG. 13(c), the capillary module 120 passes through the sealing film 117 and is introduced into the cuvette 110. When a secondary pressure is applied to the housing 140 in this state, as illustrated in FIG. 13(d), the reagent rod 130 is further moved downward, and, accordingly, the reagent rod sealing film 138 at the upper drying reagent accommodation part 132 is also stripped. Similar to the embodiment of FIG. 12, a tip of the reagent rod 130 first ruptures the sealing film 117 before a tip of the capillary module 120 does to discharge pressure generated inside the cuvette 110, and then the tip of the capillary module 120 ruptures the sealing film 117 and is introduced into the cuvette 110.

Meanwhile, high-speed rotation of the rotating body 200, which is performed to centrifuge red blood cells present in whole blood, causes vibration and noise, and problems in terms of heat generation, durability, and the like of a motor, and thus it is important to centrifuge red blood cells by low-speed rotation. In addition, when an analyte is measured using a whole blood sample, red blood cells present in the whole blood sample affect measurement. First, packed cell volumes vary according to a whole blood sample, and thus, even though the same amount of whole blood samples are used for measurement, the amount of plasma including an analyte varies. Thus, the hematocrit present in the whole blood sample is measured and the amount of plasma should be corrected. Second, red blood cells, which are a particle component, exhibit turbidity in a solution, and thus cause errors in spectrophotometry. These red blood cells are precipitated on the bottom surface of the cuvette 110, which is a centrifugal force acting surface, by centrifugal force generated when the rotating body 200 is rotated, and thus removed from the liquid reagent. To effectively precipitate red blood cells from the liquid reagent included in the cuvette 110 onto the bottom surface of the cuvette 110, which is a centrifugal force acting surface, by centrifugal force generated according to rotation of the rotating body 200, a red blood cell coagulant may be used. The red blood cell coagulant, which is a polycation, binds to red blood cells, and, accordingly, aggregation of the red blood cells occurs, and the coagulated red blood cells are easily precipitated onto the bottom surface of the cuvette 110, which is a centrifugal force acting surface, by centrifugal force generated according to rotation of the rotating body 200. In addition, the red blood cell coagulant may prevent the red blood cells from being adhered to a wall surface of the cuvette 110 in a process of being precipitated by centrifugal force, and the coagulated red blood cells precipitated on the bottom of the cuvette 110 are not easily dispersed in a liquid reagent by shaking of the liquid reagent, and thus are effectively removed therefrom.

Thus, a cationic polyelectrolyte that causes aggregation of red blood cells to increase the size of particles and, accordingly, is capable of centrifuging the red blood cells with a relatively low centrifugal force, such as poly-L-lysine, poly-L-arginine, poly-L-histidine, poly(diallyldimethylammonium chloride), poly(allylamine hydrochloride), poly(acrylamide-co-diallyldimethylammonium chloride), polyethylenimine, poly(2-dimethylamino)ethyl methacrylate) methyl chloride quaternary salt, or the like may be added to the liquid reagent of the cuvette 110. In addition, the liquid reagent may be a buffer with a pH ranging between 5.0 and 9.0.

In addition, the lower and upper drying reagent accommodation parts 131 and 132 included in the reagent rod 130 for storing a drying reagent may include a dried form of an enzyme, an antibody, or the like that reacts with or binds to an analyte in the sample, and may include a coloring dye, a chemiluminescent reagent, a fluorescent or phosphorescent reagent, or the like that reacts with an enzyme and develops color. Examples of the enzyme include glucose oxidase, glucose dehydrogenase, horseradish peroxidase, ascorbate oxidase, cholesterol esterase, cholesterol oxidase, creatine amidinohydrolase, diaphorase, glucose-6-phosphate dehydrogenase, glutamate dehydrogenase, glycerol kinase, glycerol dehydrogenase, hexokinase, D-3-hydroxybutyrate dehydrogenase, lactate dehydrogenase, lipoprotein lipase, pyruvate oxidase, alkaline phosphatase, catalase, fructosyl-amino acid oxidase, fructosyl-peptide oxidase, urease, protease, ketoamine oxidase, hexokinase (HK), and glucose-6-phosphate dehydrogenase (G-6-PDH). The type of these enzymes is not limited, and all enzymes that selectively react with an analyte present in the sample may be used.

In addition, the lower and upper drying reagent accommodation parts 131 and 132 may include a reaction product produced by a reaction between the analyte present in the sample and the enzyme, or a coloring dye, a fluorescent material, or luminescent material that is used to measure a consumable material. Such a reaction product or a consumable material may be hydrogen peroxide or NADH, and materials for measuring this may be tetrazolium derivatives; 2-(4-iodophenyl)-3-(4-nitrophenyl)-5-phenyl-2H-tetrazolium chloride (INT), 3-(4,5-dimethyl-2-thiazolyl)-2,5-diphenyl-2H-tetrazolium bromide (MTT), 3,3'-[3,3'-dimethoxy-(1,1'-biphenyl)-4,4'-diyl]-bis[2-(4-nitrophenyl)-5-phenyl-2H-tetrazolium chloride (Nitro-TB), 3,3'-[3,3'-dimethoxy-(1,1'-biphenyl)-4,4'-diyl]-bis(2,5-diphenyl-2H-tetrazolium chloride) (TB), 2-(4-iodophenyl)-3-(4-nitrophenyl)-5-(2,4-disulfophenyl)-2H-tetrazolium, monosodium salt (WST-1), 2-(4-iodophenyl)-3-(2,4-dinitrophenyl)-5-(2,4-disulfophenyl)-2H-tetrazolium, monosodium salt (WST-3), 2-benzothiazolyl-3-(4-carboxy-2-methoxyphenyl)-5-[4-(2-sulfoethylcarbamoyl)phenyl]-2H-tetrazolium (WST-4), 2,2'-dibenzothiazolyl-5,5'-bis[4-di(2-sulfoethyl)carbamoylphenyl]-3,3'-(3,3'-dimethoxy 4,4'-biphenylene)ditetrazolium, disodium salt (WST-5), 4-aminoantipyrine that reacts with hydrogen peroxide, N-ethyl-N-(2-hydroxy-3-sulfopropyl)-3-methoxyaniline, sodium salt, dehydrate (ADOS), N-ethyl-N-(3-sulfopropyl)-3-methoxyaniline, sodium salt, monohydrate (ADPS), N-ethyl-N-(3-sulfopropyl)aniline, sodium salt (ALPS), 3,3☐-diaminobenzidine, tetrahydrochloride (DAB), N-ethyl-N-(2-hydroxy-3-sulfopropyl)-3,5-dimethoxyaniline, sodium salt (DAOS), N-(2-hydroxy-3-sulfopropyl)-3,5-dimethoxyaniline, sodium salt (HDAOS), N,N-bis(4-sulfobutyl)-3,5-dimethylaniline, disodium salt (MADB), 3,3'-,5,5'-tetramethylbenzidine (TMBZ), N,N-bis(4-sulfobutyl)-3-methylaniline, disodium salt (TODB), N-ethyl-N-(2-hydroxy-3-sulfopropyl)-3-methylaniline, sodium salt (TOOS), N-ethyl-N-(3-sulfopropyl)-3-methylaniline, sodium salt (TOPS), sodium 10-(carboxymethylaminocarbonyl)-3,7-bis(dimethylamino)phenothiazine (DA-67), N-(carboxymethylaminocarbonyl)-4,4'-bis(dimethylamino)diphenylamine sodium salt (DA-64), 4-hydroxybenzoic acid, N-ethyl-N-(2-hydroxy-3-sulfopropyl)-3,5-dimethylaniline (MAOS), and the like.

In addition, the lower and upper drying reagent accommodation parts 131 and 132 may include 2,5-dichlorophenyldiazonium tetrafluoroborate (DPD), bromocresol green (BCG), o-cresolphthalein complexone, nitroblue tetrazolium (NBT), or the like that directly binds to or reacts with the analyte in the sample to develop color. In addition, the lower and upper drying reagent accommodation parts 131 and 132 may include a variety of enzyme substrates, such as p-nitrophenyl phosphate, L-alanine, α-ketoglutarate, L-aspartate, L-γ-glutamyl-3-carboxy-4-nitroanilide, glycylglycine, L-lactate, and the like. In addition, the lower and upper drying reagent accommodation parts 131 and 132 may include an antigen, an antibody, or an aptamer that selectively binds to the analyst inside the sample, and may include latex particles, gold particles, silver particles, magnetic particles, and the like, on which these materials are immobilized. In addition, the lower and upper drying reagent accommodation parts 131 and 132 may include a surfactant such as Triton X-100, bile acid, sodium cholate, Tween 20, sodium dodecyl sulfate (SDS), or the like.

According to another embodiment, a hemagglutination reagent for causing aggregation of red blood cells may be included in a drying reagent accommodation part of the reagent rod 130. A red blood cell coagulant may be included in the lower drying reagent accommodation part 131 or upper drying reagent accommodation part 132 of the reagent rod 130, preferably, in the lower drying reagent accommodation part 131. The red blood cell coagulant present in the lower drying reagent accommodation part 131 may first react with the reagent of the cuvette 110 and thus a first reaction is measured, and, in a next process, the reagent present in the upper drying reagent accommodation part 132 may reach the cuvette 110 and react therewith, and thus main measurement may be performed.

Figure 14:
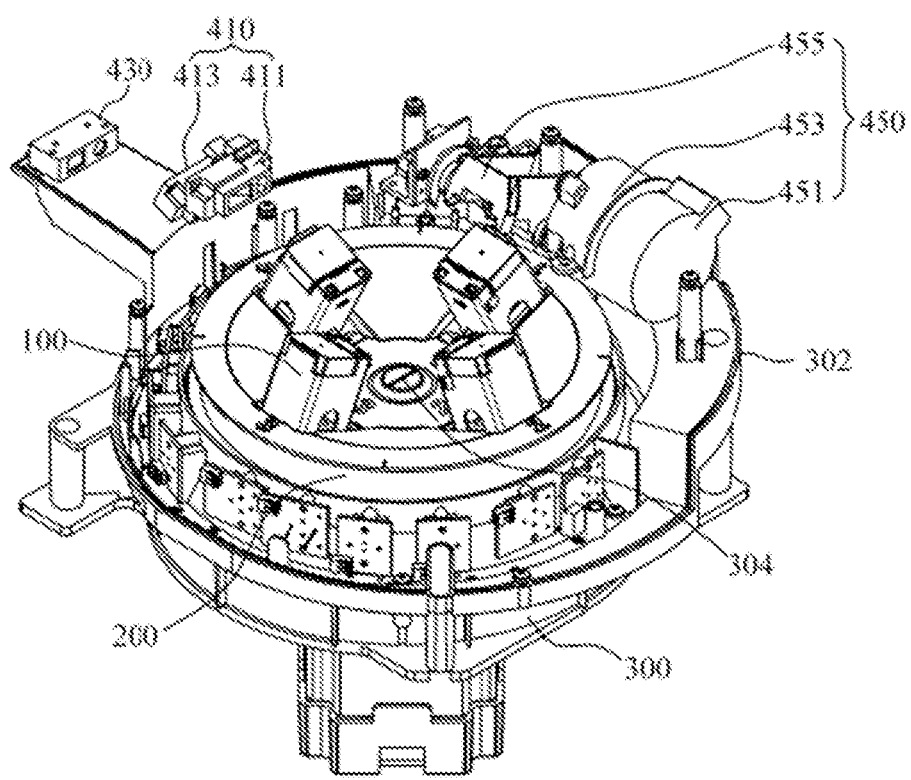
FIG. 14 is a perspective view of a bioinstrument according to another embodiment.

FIG. 14 is a perspective view illustrating a structure of a bioinstrument according to another embodiment. As illustrated in the drawing, the main body 300 of the bioinstrument may further include a cartridge detection sensor 410 installed at the main body 300 to detect whether or not a cartridge is loaded in the rotating body 200 and a loading height of the cartridge. In the illustrated embodiment, the cartridge detection sensor 410 includes two infrared sensors 411 and 413. When the cartridge holder 210 is aligned with the cartridge detection sensor 410 according to rotation of the rotating body 200, the cartridge detection sensor 410 emits infrared rays and receives reflected light, and a control module of the bioinstrument analyzes receives optical signals. If the reflected light is weak, the control module of the bioinstrument determines that the cartridge is not loaded.

In the illustrated embodiment, four cartridges may be loaded in the rotating body 200. When four cartridges are radially loaded in four cartridge holders 210, or two cartridges are loaded in two cartridge holders 210 at opposite positions, a rotation balance therebetween is obtained, and thus there is no problem with measurement. However, as a result of performing measurement at positions of the four cartridge holders 210, when the rotation balance is lost, such as when only three cartridges are loaded, only one cartridge is loaded, or two cartridges are loaded on one side instead of being radially positioned, an error message is output and measurement is stopped.

When it is determined that cartridges have been loaded, a control circuit of the bioinstrument measures a distance to the cartridges by analyzing a signal of the cartridge detection sensor 410. In a case in which cartridges are not completely inserted into the cartridge holders 210, when high-speed rotation is performed thereon, the cartridges escape therefrom and thus measurement is stopped or the bioinstrument may be damaged. The control module determines whether or not cartridges are normally and completely loaded, from information on a distance to the cartridges. In the illustrated embodiment, the cartridge detection sensor 410 includes the two infrared sensors 411 and 413. It may be more accurately determined whether or not cartridges are normally loaded by measuring a distance to the cartridges at different heights.

Referring to FIG. 14, the bioinstrument may further include a cartridge information reader 430 installed at the main body 300 to read information about a measurement cartridge recorded on one surface of the cuvette 110 installed in the rotating body 200. In one embodiment, the information about a measurement cartridge may include measurement items, validity period, calibration curve information, lot information, information about cartridge compatibility, and the like. In the illustrated embodiment, the cartridge information reader 430 is aligned with the cartridge detection sensor 410 at the same position. Information about a measurement cartridge printed on one surface of the cartridge may be read at a position for determining whether or not cartridges are normally loaded. For example, the information about a measurement cartridge may be recorded as a barcode on a surface of a cartridge. In one embodiment, the cartridge information reader 430 is a scan module for reading a barcode. In another embodiment, the cartridge information reader 430 may be a camera module. The camera module may recognize a barcode, or may be used to read information recorded as an optical character. In another embodiment, the cartridge information reader 430 may be an RF tag reader. In this embodiment, a cartridge may have at a surface thereof, an RF tag attached thereto, wherein the RF tag stores measurement cartridge information of the cartridge. According to one embodiment, the main body 300 may further include a cartridge actuator 450 installed in the enclosure 302 to drive a cartridge so that a sample or reagent of the cartridge loaded in the rotating body 200 is introduced.

Figure 15:
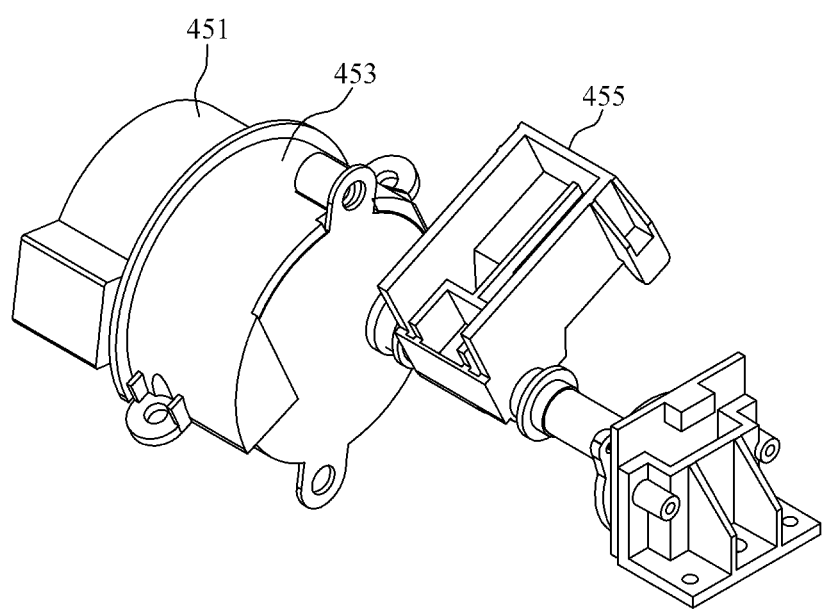
FIG. 15 is a perspective view illustrating a structure of a cartridge actuator of the embodiment of FIG. 14.

FIG. 15 is a perspective view more specifically illustrating the cartridge actuator 450. As illustrated in the drawing, the cartridge actuator 450 according to one embodiment includes a drive motor 451, a reduction gear 453, and a drive arm 455. The drive motor 451 is able to perform position control to allow adjustment of a cartridge pressing depth. A cartridge pressing speed and force may be adjusted through the reduction gear 453. The drive arm 455 has a shape corresponding to that of a head of a cartridge.

When the reagent rod 130 and the capillary module 120 are separated and independently operated, two cartridge actuators 450 may be separately configured. In a case in which the reagent rod 130 immobilizes a plurality of reagents, when driving the reagent rod 130, the cartridge actuator 450 operates in a stepwise manner at appropriate depths to correspond to the immobilized positions of the reagents.

The exemplary embodiments of the present invention have been described above. It will be understood by those skilled in the art to which the present invention pertains that the present invention may be embodied in modified forms without departing from essential characteristics of the present invention. Thus, the disclosed embodiments should be considered in an illustrative sense only and not for the purpose of limitation. The scope of the present invention is defined by the following claims, not by the foregoing description, and all differences within a range equivalent thereto should be construed as being within the scope of the present invention.

The invention claimed is:

1. A bioinstrument comprising:
a rotating body comprising a plurality of radially symmetrically positioned cartridge holders each of which is configured to hold a cartridge allowing a reaction between a reagent stored in the cartridge and an analyte in a sample to be loaded therein;
a main body comprising at least one light detector capable of receiving light from the cartridge holders and optically measuring the analyte in the sample;
a cartridge actuator installed at the main body to drive a cartridge so that the reagent of the cartridge is introduced into a cuvette of the cartridge;
a cartridge detection sensor installed at the main body to detect whether or not the cartridge is loaded in the rotating body and a loading height of the cartridge;
a motor connected to the rotating body, the motor capable of rotating the rotating body at an angular velocity sufficient to separate a particle component from the sample by centrifugal force; and
a controller configured to drive the motor to successively position each of the plurality of cartridge holders to detect presence of a respective cartridge in each of the plurality of cartridge holders by the cartridge detection sensor, to decide whether rotation balance is obtained based on the detection, and if it is decided that rotation balance is not obtained, output an error message,
wherein the rotating body comprises one or more light receiving optical waveguides, each of which guides light from each of the plurality of cartridge holders to the at least one light detector.

2. The bioinstrument of claim 1, wherein the main body further comprises at least one light source, and the rotating body further comprises one or more light emitting optical waveguides to guide light from the at least one light source to each of the plurality of cartridge holders.

3. The bioinstrument of claim 2, wherein each of the one or more light emitting optical waveguides is installed in surface contact with each of the plurality of cartridge holders to face a light irradiation surface, the light irradiation surface being one surface of the cuvette when a cartridge is mounted to the cartridge holder.

4. The bioinstrument of claim 1, wherein each of the one or more light receiving optical waveguides is installed in surface contact with each of the plurality of cartridge holders to face a light receiving measurement surface of the cuvette when a cartridge is mounted to the cartridge holder.

5. The bioinstrument of claim 3, wherein each of the one or more light receiving optical waveguides is installed in surface contact with each of the plurality of cartridge holders to face a light receiving measurement surface of the cuvette when the cartridge is mounted to the cartridge holder.

6. The bioinstrument of claim 5 further comprising a cartridge having therein the cuvette, wherein the light irradiation surface and the light receiving measurement surface of the cuvette are different surfaces.

7. The bioinstrument of claim 6, wherein the light irradiation surface and the light receiving measurement surface of the cuvette face opposite each other.

8. The bioinstrument of claim 6, wherein the light irradiation surface and the light receiving measurement surface of the cuvette are at right angles.

9. The bioinstrument of claim 1, wherein an inner wall of the cartridge holder is inclined with respect to a rotational axis of the rotating body such that the cartridge is loaded to be inclined towards an inside of the rotating body.

10. The bioinstrument of claim 1, wherein the main body further comprises a cartridge information reader installed at the main body to read information about a measurement cartridge recorded on one surface of the cartridge loaded in the rotating body.

11. The bioinstrument of claim 3, wherein the bioinstrument further comprises:
a second light source with different wavelength bands from the at least one light source; and
a second light detector;
wherein the at least one light source, the second light source, the at least one light detector, and the second light detector are installed at the main body along an outer circumference of the rotating body.

12. The bioinstrument of claim 3,
wherein the at least one light detector measures a luminance of a light receiving measurement surface of the cuvette.

13. A bioinstrument comprising:
a centrifuge main body comprising an enclosure that houses an axle and a light detector;
a centrifuge rotation body rotatably fixed to the axle of the centrifuge main body, the centrifuge rotation body comprising a plurality of radially symmetrically positioned cartridge holders, each having a surface away from the axle of the centrifuge main body;
a cartridge actuator installed in the enclosure of the centrifuge main body;
a detection optical waveguide having an input end and an output end, the input end facing a surface of one of the plurality of cartridge holders other than the surface away from the axle of the centrifuge main body, and the output end facing away from the one of the plurality of cartridge holders;
a cartridge detection sensor installed at the centrifuge main body to detect whether or not the cartridge is loaded in the centrifuge rotating body and a loading height of the cartridge;
a centrifuge motor connected to the centrifuge rotation body via the axle and capable of rotating the centrifuge rotation body at an angular velocity sufficient to separate a biological cell from a liquid biological sample by centrifugal force; and
a controller configured to align the output end of the detection optical waveguide of the centrifuge rotation body with the light detector of the centrifuge main body so that any light in the one of the plurality of cartridge holders can be detected by the light detector, and configured to drive the cartridge actuator to drive a cartridge so that a reagent of the cartridge is introduced into a cuvette of the cartridge,
wherein the controller is further configured to drive the motor to successively position each of the plurality of cartridge holders to detect presence of a respective cartridge in each of the plurality of cartridge holders by the cartridge detection sensor, to decide whether rotation balance is obtained based on the detection, and if it is decided that rotation balance is not obtained, output an error message.

14. The bioinstrument of claim 13, wherein the centrifuge main body further comprises a light source;
wherein the centrifuge rotation body further comprises a source optical waveguide having an input end and an output end, the output end facing a surface of the one of the plurality of cartridge holders other than the surface away from the axle of the centrifuge main body, and the input end facing away from the one of the plurality of cartridge holders; and
wherein the controller is further configured to align the input end of the source optical waveguide of the centrifuge rotation body with the light source of the centrifuge main body so that any light from the light source can be directed to the one of the plurality of cartridge holders.

15. The bioinstrument of claim 13, further comprising:
a cartridge removably held in at least one of the plurality of cartridge holders of the centrifuge rotation body, the cartridge comprising the cuvette having a centrifugal force acting surface farthest away from the axle of the centrifuge main body; and
a transparent surface, other than the centrifugal force acting surface, that faces the input end of the detection optical waveguide of the centrifuge rotation body.

16. The bioinstrument of claim 14, further comprising:
a cartridge removably held in at least one of the plurality of cartridge holders of the centrifuge rotation body, the cartridge comprising the cuvette having a transparent surface that faces the input end of the detection optical waveguide of the centrifuge rotation body; and
a transparent surface that faces the output end of the source optical waveguide of the centrifuge rotation body.

17. The bioinstrument of claim 13, further comprising a plurality of light detectors in the centrifuge main body,
wherein the light detector and the plurality of light detectors are respectively sensitive to different wavelength bands of light.

18. The bioinstrument of claim 14, further comprising:
a plurality of light sources in the centrifuge main body; and
a plurality of light detectors,
wherein the light source and the plurality of light sources emit a respective plurality of wavelength bands of light, and
wherein the light detector and the plurality of light detectors are sensitive to the respective plurality of wavelength bands of light.

19. The bioinstrument of claim 13, wherein the centrifuge motor is capable of driving the rotation of the centrifuge rotation body at 1,000 revolutions per minute.

20. The bioinstrument of claim 1, wherein a number of the plurality of cartridge holders is four (4), and the controller is configured to decide that rotation balance is obtained when all the four cartridge holders are occupied by the respective cartridges or two (2) radially positioned cartridge holders are occupied by the respective cartridges.

\* \* \* \* \*